United States Patent [19]

Muz et al.

[11] Patent Number: 5,610,379
[45] Date of Patent: Mar. 11, 1997

[54] LIQUID AND GAS IMPENETRABLE SWITCH

[75] Inventors: Edwin Muz, Reutlingen; Dieter Schwarz, Neubulach, both of Germany

[73] Assignee: Nicolay Verwaltungs -GmbH, Nagold, Germany

[21] Appl. No.: 594,585

[22] Filed: Jan. 31, 1996

[30] Foreign Application Priority Data

Feb. 4, 1995 [DE] Germany ................. 195 03 702.2

[51] Int. Cl.⁶ ....................................... H01H 13/00
[52] U.S. Cl. .............................. 200/552; 200/302.3
[58] Field of Search ............... 200/302.3, 302.2, 200/302.1, 516, 517, 5 A, 5 E, 552, 528

[56] References Cited

U.S. PATENT DOCUMENTS

| | | |
|---|---|---|
| 3,801,766 | 4/1974 | Morrison . |
| 3,911,241 | 10/1975 | Jarrard . |
| 4,034,761 | 7/1977 | Prater . |
| 4,105,882 | 8/1978 | Ulbing et al. .................... 200/302.3 |
| 4,356,367 | 10/1982 | Moldenhauer ..................... 200/552 |
| 4,427,006 | 1/1984 | Nottke .............................. 200/302.2 |
| 4,520,247 | 5/1985 | Pancook et al. ................. 200/529 |
| 4,545,375 | 10/1985 | Cline .............................. 200/302.2 |

FOREIGN PATENT DOCUMENTS 3809770  10/1989  Germany .

Primary Examiner—David J. Walczak
Attorney, Agent, or Firm—Roylance, Abrams, Berdo & Goodman, L.L.P.

[57] ABSTRACT

A liquid and gas impenetrable switch, especially for electrical surgical instruments, has two pairs of contacts spaced from one another. The movable contact element of each pair is arranged between the associated fixed contact element and a diaphragm. With elastic deformation, the diaphragm and movable contacts can be moved by the switch operating force into contact with the fixed contact elements. The diaphragm covers the movable contact elements and is supported by a rocker.

14 Claims, 3 Drawing Sheets

LIQUID AND GAS IMPENETRABLE SWITCH

FIELD OF THE INVENTION

The present invention relates to a liquid and gas impenetrable switch, especially for electrical surgical instruments. The switch has two pairs of fixed and movable contacts with the movable contacts being between the fixed contacts and a diaphragm supported by a rocker.

BACKGROUND OF THE INVENTION

Manual controls or handles made of insulating material are used in electrical surgical instruments. The manual control carries a metal electrode on one end. The electrode is connected with a high frequency generator through a cable inserted at the other end of the manual control. The manual control is provided with one or two finger switches so that the surgeon guiding the manual control can connect the high frequency voltage or can switch between operations, for instance, of cutting and coagulation. Switches of this type, however, are required not only in such manual controls, but also used, for example, in the case of surgical instruments for minimally invasive surgery.

Since such surgical instruments are washed and sterilized with water vapor following use, the switches are installed in an insulated housing. The housing guarantees the safety of patients and surgeons, and prevents any penetrating leakage of water.

Such a housing also incorporates a conventional switch of the type disclosed in U.S. Pat. No. 3,911,241. That switch uses a fixed contact element common to both switches and two flat spring-like movable contact elements. When no operational force is exerted on the movable contact elements, they are held by two insulating bodies mounted on their end segments at some distance from the fixed contact element. Each of the surface areas of the insulated housing aligned with the movable contact elements forms an elastically deformable diaphragm. Through those areas, the movable contact elements can be bent down against the fixed contact element far enough to contact it.

Disadvantageously, the two switches can be connected simultaneously. Additionally, the plastics used for the insulated housing, such as silicon rubber or thermoplastic elastomers, cannot prevent gas diffusion into the interior of the housing at the temperature at which the sterilization occurs. Since the insulated housing is compressed by the pressure of the water vapor in the areas of the two diaphragms, such pressure closes the contacts of both switches. Following the sterilization and cooling, a very long time can be required until both switches are again opened and again able to function, since with this arrangement the diffusion processes run for considerably longer and the pressure differential is lower than during the sterilization.

SUMMARY OF THE INVENTION

Objects of the present invention are to provide a switch which is liquid and gas impenetrable, especially for electrical surgical instruments, which has two pairs of independently operable contacts, which, upon sterilization, does not lose its capacity to function, and particularly, which is immediately ready for operation following the sterilization.

The foregoing objects are basically obtained by a switch which is liquid and gas impenetrable, especially for electrical surgical instruments, comprising first and second pairs of contacts spaced at a distance from each other, an elastically deformable diaphragm, switch operating means and a rocker. Each contact pair has a movable contact and a fixed contact. The diaphragm covers the movable contacts, locating the movable contacts between the diaphragm and the fixed contacts. The switch operating means exerts forces on the diaphragm to move the movable contacts into engagement with the fixed contacts. The rocker supports the diaphragm.

By the rocker supporting the diaphragm, the rocker compensates for the pressure forces effective in the operational area of the two switches. In this manner, the two switches remain in opened states during sterilization and are completely capable of operation immediately following termination of the sterilization. Another advantage of the switch according to the present invention is provided by the rocker precisely defining the point at which the operational force is applied on each of the two movable contact elements. A precisely applied force is not the case when the operational force is transferred directly through the diaphragm to the movable contact element. The rocker also guarantees, without additional outlay, that only one of the two switches can be connected or activated at any one time.

In one preferred embodiment, the rocker is supported between the two fixed contacts on a bearing element which supports the two fixed contacts. Because of the rocker's relatively rigid or bend-resistant construction, the rocker reliably precludes simultaneous movements of the two rocker end segments toward the fixed contacts. The rocker, for instance, can be supported on the bearing element by a pivot which is installed in a middle location between the two fixed contacts on the bearing element. The rocker is supported at its midpoint.

In one preferred embodiment, the bearing element is a conductor plate. This is the simplest arrangement to facilitate production of the required electric connections.

The two movable contacts are preferably formed by the two end segments of a spring, with the spring middle segment securely mounted on the conductor plate. Two end segments of the flat spring can each form a hemispherical segment, with the free border or edge of each hemispherical segment supported on the conductor plate. In this manner, it is easy to attain a transient closing of the switch.

The spring can be fastened to the conductor plate by a bolt welded with the conductor plate, and can be connected electrically conductively with one of the conductive paths printed on the conductor plate. This bolt can advantageously form the pivot element for the rocker. These measures contribute to lowering the cost for the switch. Lower cost is also provided by forming each fixed contact by one contact pin.

The contact elements and the rocker are preferably arranged in the interior chamber of a plastic housing. The interior is closed off by the diaphragm on the side serving the switch operation. The diaphragm can be constructed in one integral or unitary piece with the plastic housing. Contact terminals can also be constructed integral with this closed plastic housing. The terminals can be connected with the conductive paths of the conductor plate. These contact terminals can fit into a recess of the plastic housing open to the outside, so that a plug socket is formed for receiving a plug adapted to be inserted in the recess.

The switch according to the present invention can be located in the handle part of an instrument or the like. It is preferably arranged in an inherently stable casing which is non-deformable. The rocker is aligned with movable switch operating buttons which are guided slidably in the casing to cause engagement of the contacts.

Other objects, advantages and salient features of the present invention will become apparent from the following detailed description, which, taken in conjunction with the annexed drawings, discloses preferred embodiments of the present invention.

BRIEF DESCRIPTION OF THE DRAWINGS

Referring to the drawings which form a part of this disclosure.

DETAILED DESCRIPTION OF THE INVENTION

A handle of an electrical surgical instrument has a non-deformable or relatively rigid casing 1. Casing 1 is essentially in the shape of a cylindrical rod, with both of its end segments tapering toward the ends. A partially illustrated electrode 2 exits the casing at one end. An electrical conductor 3 extends from the other end of the casing for connecting electrode 2 with a high frequency energy source.

Figure 1:
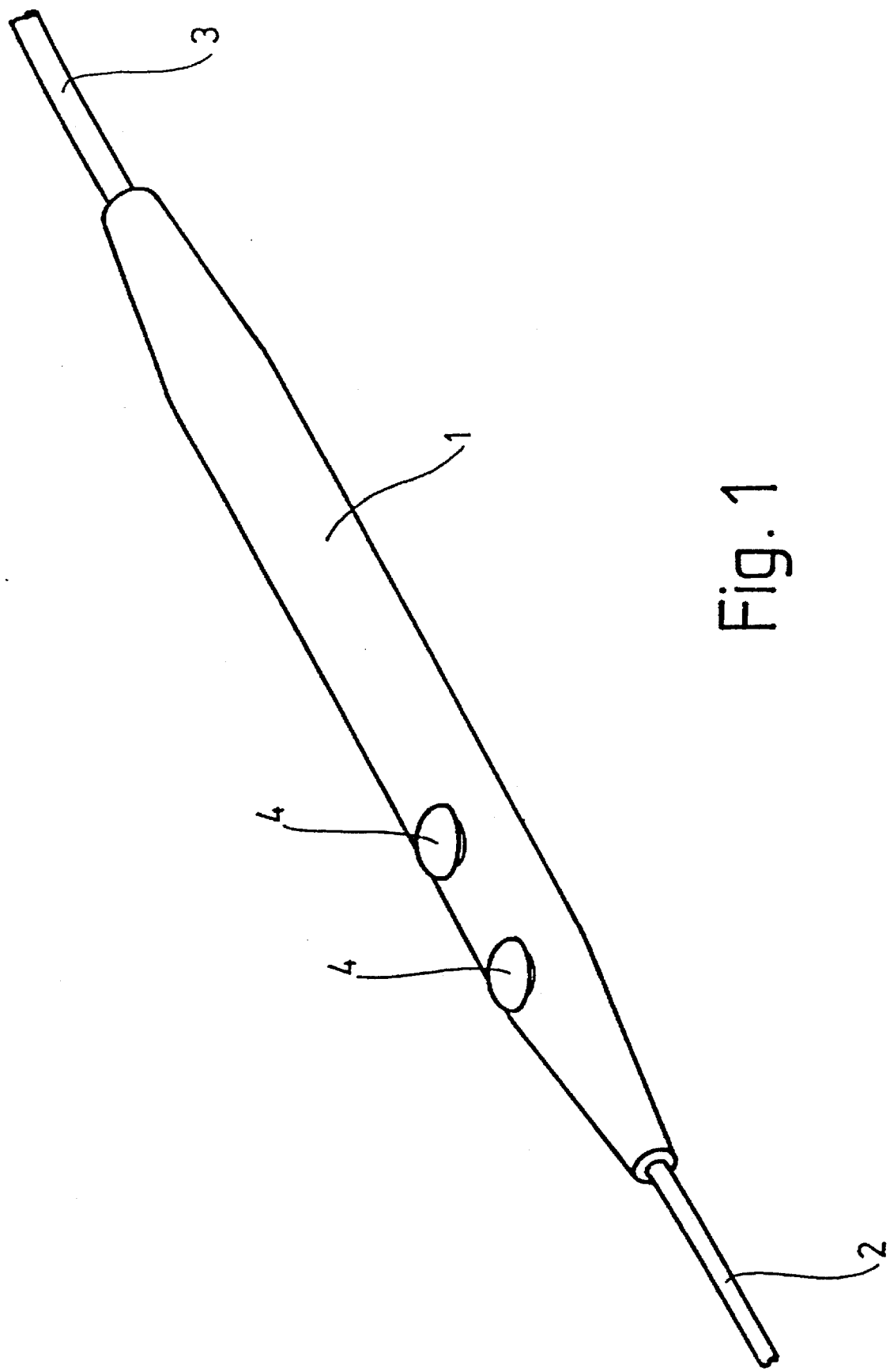
FIG. 1 is a perspective view of a switch according to a first embodiment of the present invention, including the handle element of a surgical instrument.
Figure 2:
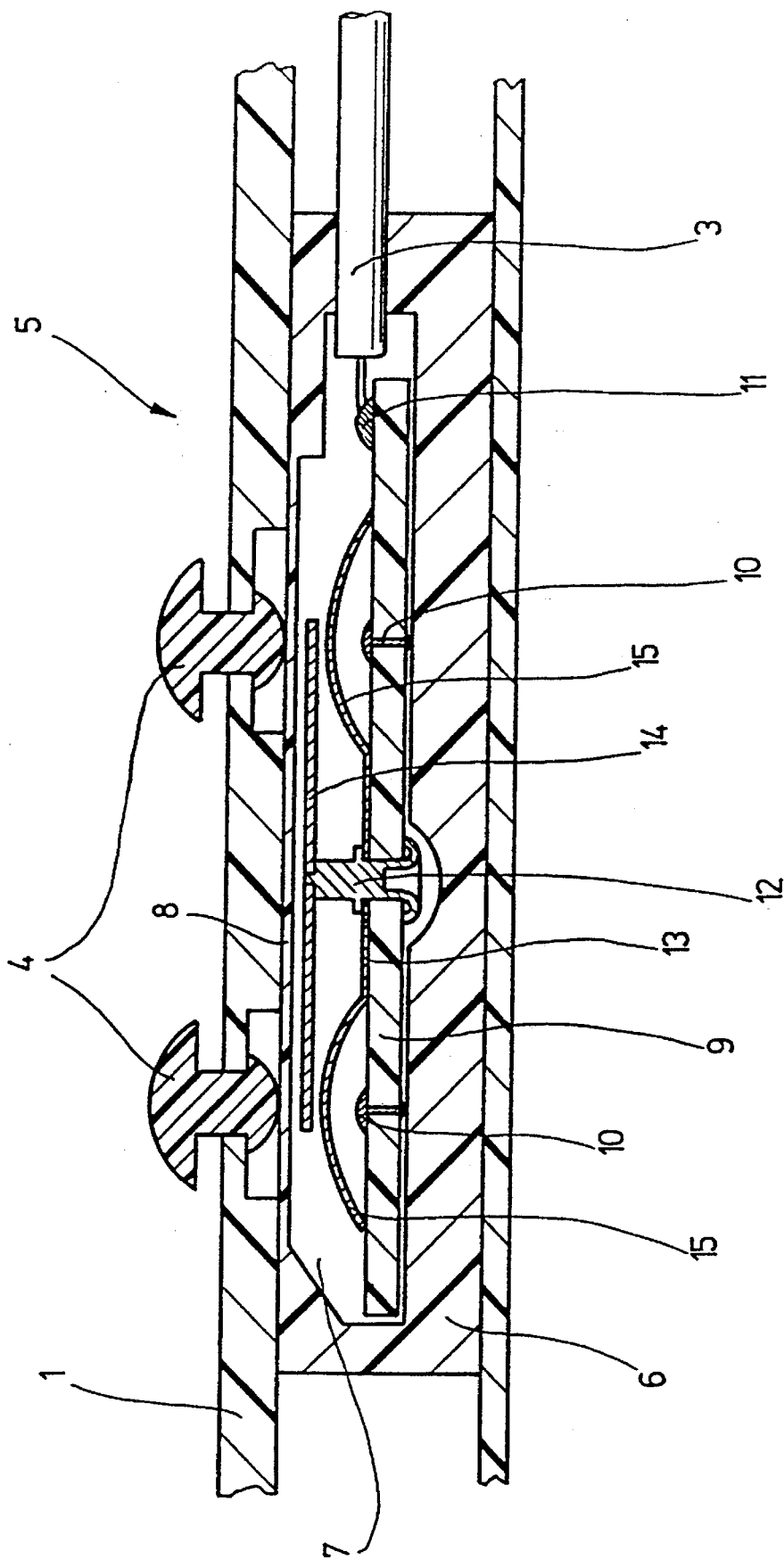
FIG. 2 is a partial and enlarged side elevational view in section of the handle element of FIG. 1.

In the handle area of casing 1, two switch operating buttons 4 are arranged at some distance from one another and are aligned along the longitudinal axis of the casing, as is shown in FIG. 2. Each button is slidably guided in a radial direction of the casing in a guide bore. By virtue of cutouts on the interior side of casing 1, with each cutout being concentric with one of the two guide bores, the buttons do not project beyond the interior wall surface of casing 1 when not in operational or activated state.

In the segment of casing 1 including both switch operating buttons 4, a liquid and gas impenetrable switch 5 is arranged. Switch 5 incorporates a plastic housing 6 engaged on the interior wall of casing 1. Housing 6, in this embodiment, is formed of silicon rubber. It also, for example, could be of a thermoplastic elastomer. Plastic housing 6 is sealed on all sides. An interior chamber 7, in plastic housing 6, is defined by and limited to the area aligned with the two switch operating buttons 4 and limited by an elastically deformable diaphragm 8. Diaphragm 8 is configured as one integral or unitary piece with plastic housing 6.

A conductor plate 9 is securely fastened on the other side of interior chamber 7, opposite diaphragm 8. Conductor plate 9 is aligned with the two switch operating buttons 4, and supports a contact pin 10 for each button as the solid or fixed contact of each of the two contact pairs. Contact pins 10 are electrically connected with soldered connection elements 11 located at one end of conductor plate 9 through conductive paths leading to the rear of conductor plate 9. The conductive paths are located at the side of plate 9 remote from diaphragm 8.

Midway between the two contact pins 10, conductor plate 9 is pierced through by a bolt 12. Bolt 12 connects a spring 13, on the conductor plate side facing toward the diaphragm, tightly with conductor plate 9. On its other side, bolt 12 is connected electrically and conductively with a conductive path. Bolt 12, in the illustrated example, is welded to conductor plate 9 and projects above the plate on its side facing toward diaphragm 8. As FIG. 2 illustrates, it ends at some distance from diaphragm 8 and serves as pivot for a metal, bend-resistant or substantially rigid rocker 14. The rocker, in this embodiment, has the shape of a flat bar with two lever arms of identical length. The lever arms extend into the areas between the switch operating buttons 4 and the contact pins 10.

Two identically configured hemi-spherical end segments 15 are connected by the flat middle segment of spring 13 which is engaged on conductor plate 9. Each hemispherical segment 15 is aligned with the associated contact pin 10. When the switch is opened, each end segment rests with its border on conductor plate 9.

Three wires from electrical conductor 3 are connected with the three soldered connection elements 11. The conductor extends tightly through the one working surface of plastic housing 6.

When one of the two switch operating buttons 4 is pressed, its spherical interior head deforms diaphragm 8. Through the diaphragm, one interior head engages the respective end segment of rocker 14 to move that rocker end segment into contact with one of the two movable contact elements 15, which contact elements are formed by the two hemi-spherical end segments of spring 13. Rocker 14 then engages a defined point of the respective movable contact element 15. Further movement of rocker 14 toward the respective contact pin 10 causes the movable contact element 15 to deform resiliently and transiently into a convex shape in the direction of the contact pin 10. This action produces contact between the respective contact element 15 and contact pin 10. Any further movement of the end segment of rocker 14 toward contact pin 10 is prevented by the outer head of switch operating member 4 engaging the outer surface of casing 1. Release of button 4 allows all parts to return to the original positions shown in FIG. 2.

Simultaneous operation of the two switch operating buttons 4 in the same direction in such a manner as to yield a modification of the switch state is not possible. Diaphragm 8 engages rocker 14 in the area of the two switch operating buttons 4, and thus, prevents operation of the two movable contact elements 15 at the same time. Switch operation is likewise prevented, if during sterilization, diaphragm 8 is pressed inwardly in the direction toward conductor plate 9 by vapor pressure. Following a slight deformation, the diaphragm comes into contact with both end segments of rocker 14, which prevents any further diaphragm deformation and pivoting of the rocker. All contact pairs in this case remain in opened state, so that the switch is ready for operation immediately following sterilization.

Figure 3:
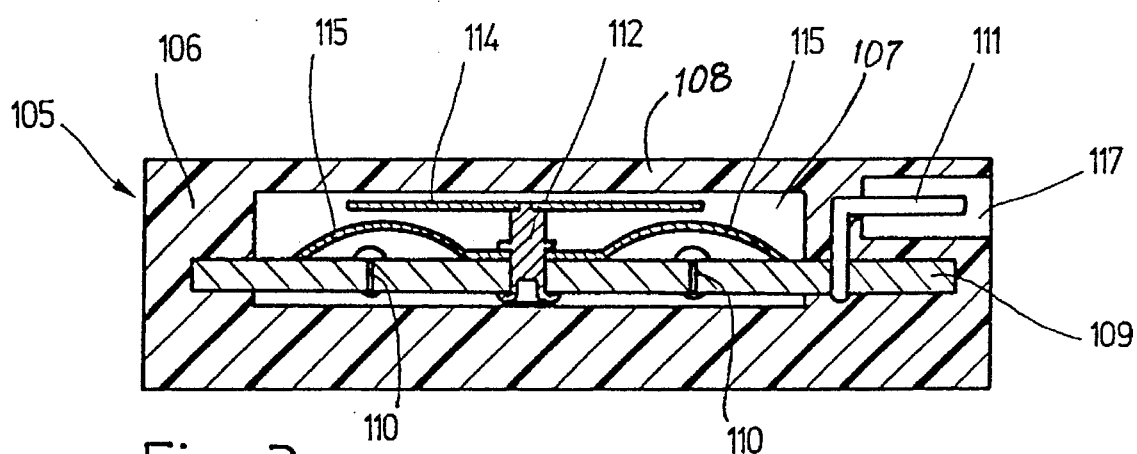
FIG. 3 is a side elevational view in section of a switch according to a second embodiment of the present invention.
Figure 4:
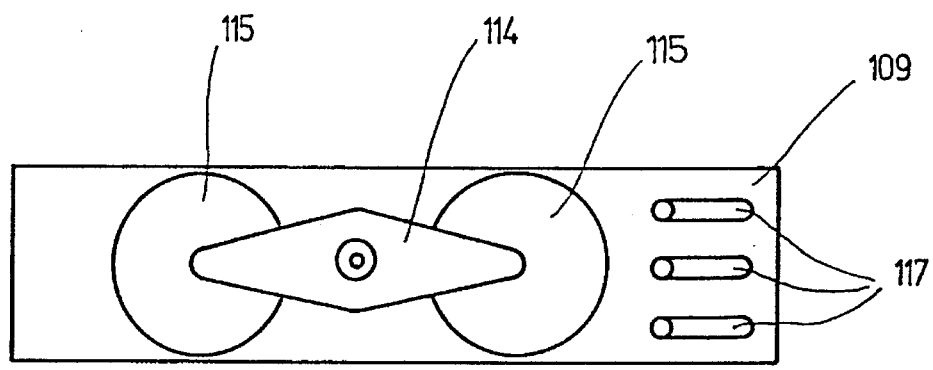
FIG. 4 is a top plan view of the conductor plate of the switch of the second embodiment, with the contact elements supported thereon.
Figure 5:
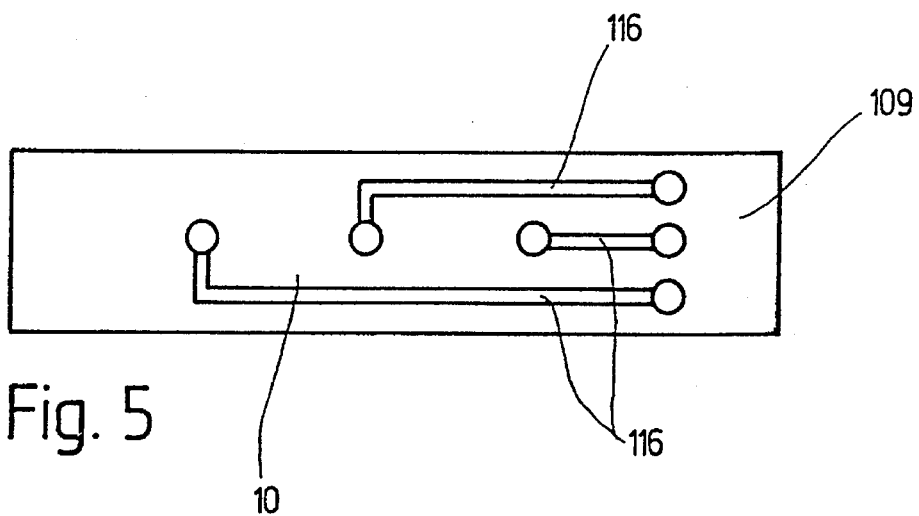
FIG. 5 is a bottom plan view of the conductor plate of FIG. 4.

The second embodiment of the switch according to the present invention, shown in FIGS. 3–5, coincides for the most part with the first embodiment. Corresponding parts are referenced with the same reference numbers increased by one hundred. Only the differences are described.

The conductor plate 109 is mounted in the interior chamber 107 of plastic housing 106. The plate forward and rear segments are embedded in the forward and rear walls of plastic housing 6. Instead of soldered connection elements 11, contact terminals 111 are connected integrally with conductor plate 109. The terminals, on one end of each terminal, contact the conductive paths 116 provided on the bottom of conductor plate 109. On the other end of each terminal, the terminals extend through the wall of plastic housing 106 and into a cutout 117 which opens to the outside. The cutout and housing form a plug socket for connection with a correspondingly constructed plug.

Rocker 114 is diamond-shaped, tapering from its middle outward. The middle of rocker 114 is mounted on bolt 112. Rocker 114 becomes uniformly and progressively narrower toward its two ends.

As in the first embodiment, rocker 114 prevents any switch operation from occurring during sterilization as a result of pressure working on diaphragm 108, because rocker 114 actually supports diaphragm 108. Also, rocker 114 guarantees that only one of the two contact pairs can be brought in contact with each other.

While various embodiments have been chosen to illustrate the invention, it will be understood by those skilled in the art that various changes and modifications can be made therein without departing from the scope of the invention as defined in the appended claims.

What is claimed is:

1. A switch which is liquid and gas impenetrable for sterilizable instruments, comprising:

first and second pairs of contacts spaced at a distance from each other, each of said contact pairs having a movable contact and a fixed contact;

an elastically deformable diaphragm covering said movable contacts such that said movable contacts are between said diaphragm and said fixed contacts;

switch operating means for exerting forces on said diaphragm to move said movable contacts into engagement with said fixed contacts; and a rigid rocker supporting said diaphragm and pivotally mounted relative to said contacts, said movable contacts being entirely located on only one side of said rocker remote from said diaphragm and said switch operating means to prevent simultaneous activation of both of said contact pairs.

2. A switch according to claim 1 wherein said fixed contacts are mounted and spaced on a bearing element;

said rocker is mounted on a support coupled to said bearing element between said fixed contacts.

3. A switch according to claim 2 wherein said rocker is bend-resistant.

4. A switch according to claim 3 wherein said support comprises a pivot means for pivotally supporting said rocker at a middle length part thereof.

5. A switch according to claim 2 wherein said bearing element comprises a conductor plate.

6. A switch according to claim 5 wherein said movable contacts comprise two end segments of a spring, a middle segment of said spring being mounted on said conductor plate.

7. A switch according to claim 6 wherein said end segments of said spring are substantially hemispherical and comprise free edges which rest on said conductor plate when not activated.

8. A switch according to claim 6 wherein said spring is coupled to said conductor plate by a bolt;

said bolt is welded to said conductor plate; and said bolt comprises a pivot element supporting said rocker.

9. A switch according to claim 5 wherein said fixed contacts comprise first and second contact pins mounted in said conductor plate; and said conductor plate comprises conductive paths connected to said contact pins.

10. A switch according to claim 1 wherein said contacts and said rocker are located in an interior chamber of a plastic housing, said interior chamber being sealed on a side thereof adjacent said switch operating means by said diaphragm, said diaphragm being a integral part of said plastic housing.

11. A switch according to claim 10 wherein contact terminals extend through said plastic housing, said terminals being electrically connected to said contacts by conductive paths.

12. A switch according to claim 11 wherein said plastic housing comprises a cutout exposed exteriorly on said plastic housing, said contact terminals projecting into said cutout.

13. A switch according to claim 10 wherein said plastic housing is arranged in a non-deformable casing; and said switch operating means comprise operating buttons slidably movable in said casing along axes aligned with said first and second pairs of contacts.

14. A switch according to claim 13 wherein said casing comprises a rod-shaped handle of an electrical surgical instrument.

\* \* \* \* \*